United States Patent [19]

Bassett

[11] Patent Number: 5,759,206

[45] Date of Patent: Jun. 2, 1998

[54] APPARATUS FOR MOUNTING A PROSTHESIS OR THE LIKE

[76] Inventor: David E. Bassett, 1850 Lakeshore Dr., Lodi, Calif. 95242

[21] Appl. No.: 530,411

[22] Filed: Sep. 18, 1995

[51] Int. Cl.⁶ .................................................. A61F 2/74
[52] U.S. Cl. ........................ 623/27; 623/38; 403/59; 403/83; 403/113
[58] Field of Search .................... 623/27, 28; 403/59, 403/83, 113

[56] References Cited

U.S. PATENT DOCUMENTS

| | | |
|---|---|---|
| 3,659,294 | 5/1972 | Glabiszewski . |
| 4,969,911 | 11/1990 | Greene . |
| 5,013,325 | 5/1991 | Rennerfelt . |
| 5,047,063 | 9/1991 | Chen . |
| 5,137,535 | 8/1992 | Keller . |
| 5,226,918 | 7/1993 | Silagy et al. . |
| 5,507,837 | 4/1996 | Laghi ........................ 623/38 |
| 5,529,576 | 6/1996 | Lundt et al. ............... 623/27 |
| 5,545,230 | 8/1996 | Kinsinger et al. ......... 623/38 |
| 5,549,710 | 8/1996 | Vera et al. ................. 623/27 |

FOREIGN PATENT DOCUMENTS

9115169  10/1991  WIPO ........................ 623/38

*Primary Examiner*—Paul B. Prebilic
*Attorney, Agent, or Firm*—Worrel & Worrel

[57] ABSTRACT

An apparatus for mounting a prosthesis or the like on an appendage of the human body, the apparatus having a first assembly adapted to be mounted on the prosthesis; a second assembly adapted to be mounted on the appendage; and an adjustment assembly operable to link the first assembly and the second assembly for selective adjustment, relative to a predetermined axis of reference, in both lateral deviation and angulation.

2 Claims, 6 Drawing Sheets

FIG. 6 though 5,759,206

APPARATUS FOR MOUNTING A PROSTHESIS OR THE LIKE

BACKGROUND OF THE INVENTION

1. Field of the Invention

The present invention relates to a mounting apparatus and, more particularly, to such a mounting apparatus which is particularly well suited to usage in uniting a pair of work objects in fixed relation to each other and relative to a plurality of reference axes.

2. Description of the Prior Art

A variety of problems are associated with the uniting of a pair of work objects in a selected relationship and particularly where adjustment may be required to achieve the optimum attitudinal relationship desired. These problems are acute in such environments in which the parameters of such adjustment are not necessarily in accordance with entirely objective considerations.

For example, in the mounting of a prosthesis on the remaining arm or leg of a human being, optimum adjustment may not conform to entirely objective standards. In other cases where objective standards exist, they may be very difficult to achieve. In this particular environment, where one of the work objects is an artificial limb and the other of the work objects is an appendage of the human body, there are both purely anatomical considerations as well as more subjective considerations to be contemplated. The anatomical considerations, in and of themselves, can involve an exceedingly complex combination of relational adjustments. Furthermore, these adjustments are influenced, to one degree or another, by such factors as the size of the person, the weight of the person, the length of the prosthesis, the point of attachment on the appendage and the like. These factors bear upon achieving proper adjustment relative to a plurality of axes of reference which are entirely interrelational. These complexities become more arcane, when the more subjective considerations, such as the comfort of the person, are taken into account.

In this particular operative environment, there are still other difficulties which arise to chronic proportions. For example, even if the most appropriate interrelational adjustments are known, achieving these adjustments under the limitations of conventional devices, is very difficult, aggravating and, in the end, frequently not achieved. Principally, the difficulty in this regard arises from the fact that conventional devices, in requiring adjustment relative to a plurality of axes of reference, are substantially incapable of maintaining one adjustment which has successfully been achieved, during the performance of successive adjustment. As a consequence, the adjustments must be repeated until, in the optimum situation, the readjustments achieve settings which conform to the desired tolerances relative to all of the settings. As a practical matter, this is extremely difficult, if not impossible, and a less than optimum compromise of the desired settings is frequently the result.

Still other problems experienced in conventional devices for attaching prostheses are encountered in their usage once attached. The complex combination of settings required inherently have, in conventional devices, resulted in an inability to maintain the settings during usage. The forces which are continually applied to the devices during use cause the settings to deviate from those originally selected and frequently result in failure of the devices. Once the settings deviate from the desired tolerances, readjustment of the settings entails all of the difficulties heretofore recited. Furthermore, the discomfort, annoyance, and loss of time experienced with such conventional devices frequently exceeds the patience of the user and may result simply in an abandonment of the prosthesis.

Therefore, it has long been known that it would be desirable to have a mounting apparatus which is particularly well suited to usage in the uniting of a pair of work objects in fixed relation to each other while being readily adjustable relative to a plurality of individual axes of reference; which is particularly well suited to usage in environments such as in the attachment and precise adjustment of prostheses; which permit adjustment of the prosthesis relative to the appendage upon which it is being mounted relative to a plurality of individual axes of reference rapidly, dependably and within a range of tolerances not heretofore achieved; which can be employed to maintain a given set of settings during usage over a prolonged period of time under the forces commonly experienced in such usage; which is of light weight and easily manipulated in the process of attachment, adjustment and removal; and which is otherwise entirely successful in achieving its operational objectives.

SUMMARY OF THE INVENTION

Therefore, it is an object of the present invention to provide an improved mounting apparatus.

Another object is to provide such a mounting apparatus which is particularly well suited to uniting a pair of work objects permitting them to be adjusted relative to each other in reference to a plurality of individual axes of reference.

Another object is to provide such a mounting apparatus which is uniquely well suited to the mounting of prostheses, such as artificial limbs, on appendages of the human body.

Another object is to provide such a mounting apparatus which permits precise adjustment of the prosthesis relative to the appendage, both as to anatomical considerations, as well as relative to more subjective considerations such as the comfort of the user.

Another object is to provide such a mounting apparatus which permits such variables as weight, size, dexterity, and other personal variables to be taken into account precisely and dependably in the adjustment of the prosthesis at the time of attachment.

Another object is to provide such a mounting apparatus which permits a precision of adjustment not heretofore achieved in the art while being both dependable and convenient in use.

Another object is to provide such a mounting apparatus which is operable to maintain the precise adjustments selected within their respective ranges of tolerances relative to a plurality of individual axes of reference without degradation due to the forces exerted thereon during use.

Another object is to provide such a mounting apparatus which is light in weight, comfortable in use and otherwise entirely satisfactory to the user thereof.

Further objects and advantages are to provide improved elements and arrangements thereof in an apparatus for the purpose described which is dependable, economical, durable and fully effective in accomplishing its intended purposes.

These and other objects and advantages are achieved, in the preferred embodiment of the present invention, in a mounting apparatus for uniting a first work object and a second work object, the apparatus having a first assembly adapted to be mounted on the first work object; a second assembly adapted to be mounted on the second work object; and an adjustment assembly operable to link the first assembly and the second assembly for selective adjustment, relative to a predetermined axis of reference, in both lateral deviation and angulation.

DESCRIPTION OF THE PREFERRED EMBODIMENT

Figure 1:
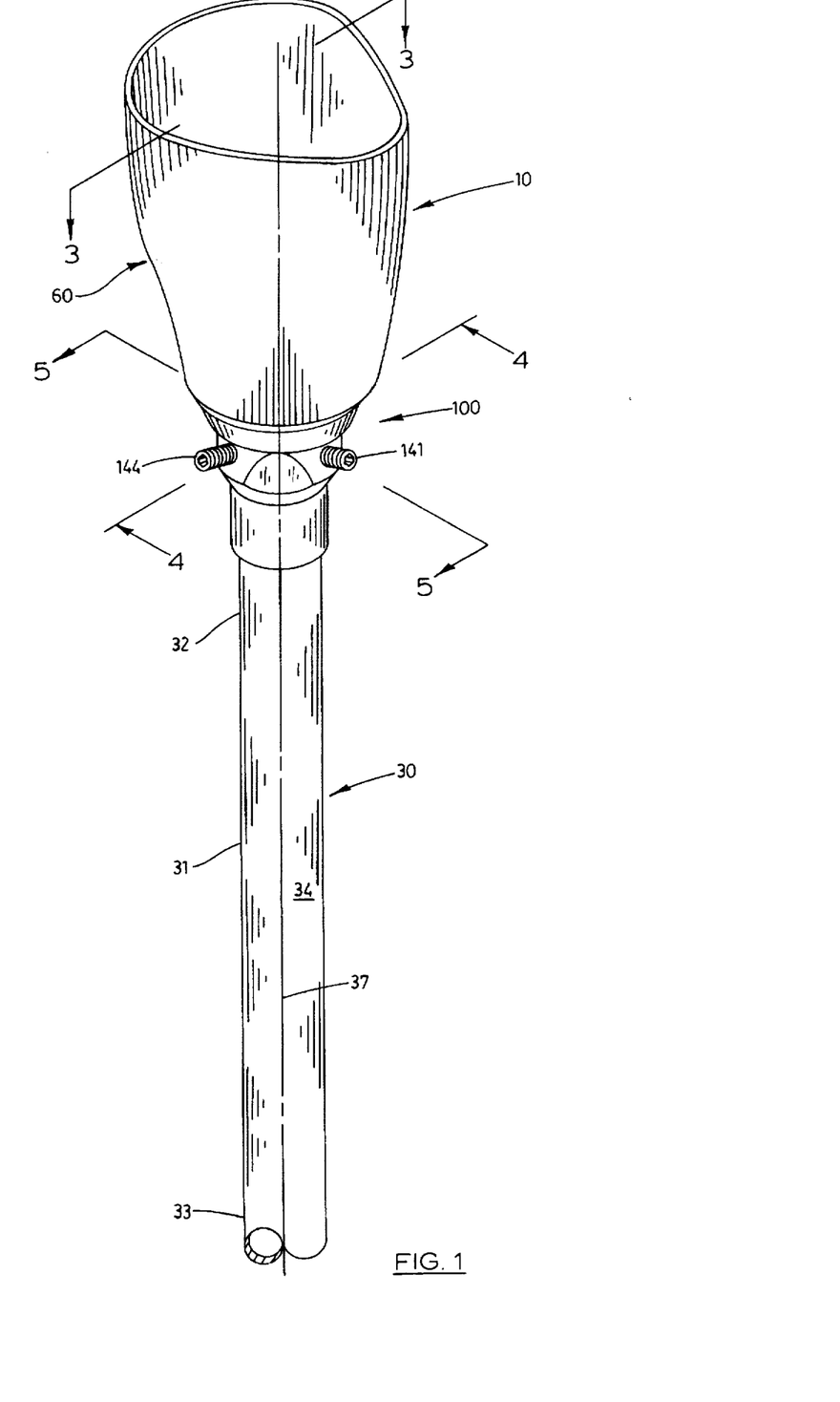
FIG. 1 is a fragmentary perspective view of the mounting apparatus of the preferred embodiment of the present invention.

Referring more particularly to the drawings, the mounting apparatus of the present invention is generally indicated by the numeral 10 in FIG. 1. While the mounting apparatus of the present invention is adaptable for use in a wide variety of operative environments, it has particular utility in uniting a pair of work objects in such a manner that they can be adjusted relative to each in reference to a plurality of individual axes of reference, as will hereinafter become more clearly apparent.

In the preferred embodiment, the mounting apparatus 10 is in a form adapted for mounting a prosthesis on an appendage of the human body. For illustrative convenience, more specifically, the mounting apparatus is shown and described herein for mounting an artificial foot and leg on the terminus of the portion of a leg remaining after amputation. Thus, for illustrative convenience in the illustrative environment, a human being 11 has a leg or appendage 12 extending to a terminus or stump 13. The appendage has an outer surface 14. In accordance with conventional practice, a sleeve 15, such as a heavy fabric or plastic sock, or the like, is extended over the terminus and disposed in closely fitted relation conforming to the shape of the terminus. This may be achieved in conjunction with the use of a sealant or antibacterial cream topically applied to the terminus prior to the positioning of the sleeve 15 thereabout. For illustrative convenience, the appendage can be viewed as having a longitudinal axis 16.

The mounting apparatus 10 includes a lower or shank assembly 30 preferably constructed of a light weight metal and having an upper end portion 32 and an opposite lower end portion 33. It will be understood that lower end portion 33 mounts an artificial foot, not shown, which, in any case, does not constitute part of the present invention. The tubular shaft 31 has a cylindrical exterior surface 34 and a cylindrical interior surface 35 bounding a passage 36. The tubular shaft has a longitudinal axis 37.

Figure 4:
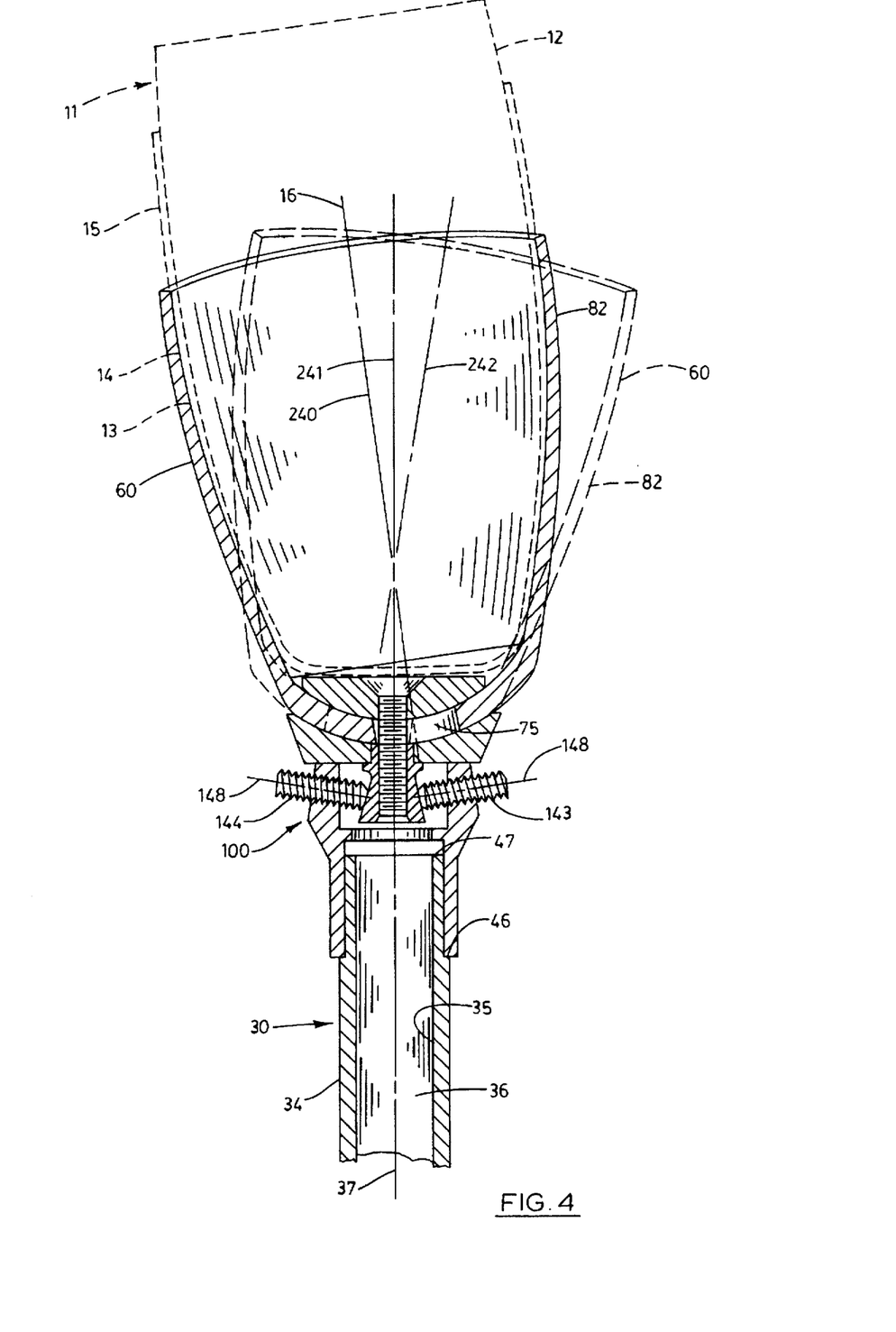
FIG. 4 is a somewhat enlarged, fragmentary, vertical section taken on line 4—4 in FIG. 1.

As best shown in FIG. 4, the upper end portion 32 of the tubular shaft 31 has a reduced cylindrical surface 45 extending to and circumscribed by an annular seat 46. The upper end portion 32 of the tubular shaft terminates in an annular surface 47 defining a plane disposed at right angles to the longitudinal axis 37.

The mounting apparatus 10 has a prosthetic mounting socket or socket assembly generally indicated by the numeral 60. The socket assembly has a socket wall 61 extending downwardly to a base wall 62. The socket assembly, composed of the socket and base walls, can be constructed of any suitable material. In the preferred embodiment, the socket assembly is constructed of rigid plastic molded to the particular configuration adapted to fit the terminus 13 and lower appendage 12. The base wall has a convex exterior hemispherical surface 63 bounded by a perimeter 64. The base wall has a concave interior hemispherical surface 65 bounded by a perimeter 66.

A central passage 75, preferably of a circular configuration, extends through the base wall 62 substantially centrally thereof. The central passage is preferably of a predetermined relatively large diameter, as will hereinafter be described in greater detail. The passage is bounded by a cylindrical surface 76. The cylindrical surface has an upper annulus 77 coextensive with the interior surface 65 and a lower annulus 78 coextensive with the exterior surface 63.

The socket wall 61 further includes a side wall 82 having an exterior surface 83 and an interior surface 84 bounding a chamber 85. The side wall extends to an upper annulus 86 bounding a mouth 87 communicating with the chamber 85. As previously noted, the dimension and configuration of the chamber 85 and mouth 87 are adapted closely to conform to the outer surface 14 of the terminus 13 of the appendage 12.

The mounting apparatus 10 has an adjustment, or linking, assembly generally indicated by the numeral 100. The linking assembly includes an adjustment housing 101 having a lower cylindrical portion 102. The cylindrical portion has an exterior surface 103 and a cylindrical interior surface 104 bounding a passage 105. The cylindrical portion 102 extends to an annulus 106 defining a plane right-angularly related to the longitudinal axis 37. Within the passage 105, the cylindrical portion terminates in an annular surface 107 also defining a plane disposed at right angles to the longitudinal axis 37.

The adjustment housing 101 has a head portion 115 which is integral with the cylindrical portion 102. The head portion has a downwardly convergent surface 116 joining the cylindrical portion 102 and an upper peripheral surface 117. The upper peripheral surface terminates in an upper planar surface 118 which defines a plane right-angularly related to the longitudinal axis 37. The head portion has an interior surface 119 bounding a chamber 120 best shown in FIGS. 2 and 6.

An interior wall 125 extends inwardly of the adjustment housing 101 separating, in effect, the chamber 120 from the passage 105. The interior wall has an upper surface 126 defining a plane right-angularly related to the longitudinal axis 37. The lower surface of the interior wall is in fact annular surface 107 constituting the terminus of the passage 105. A cylindrical surface 128 defines a passage 129 extending through the interior wall to interconnect the chamber and the passage 105 concentric to the longitudinal axis 37.

Figure 2:
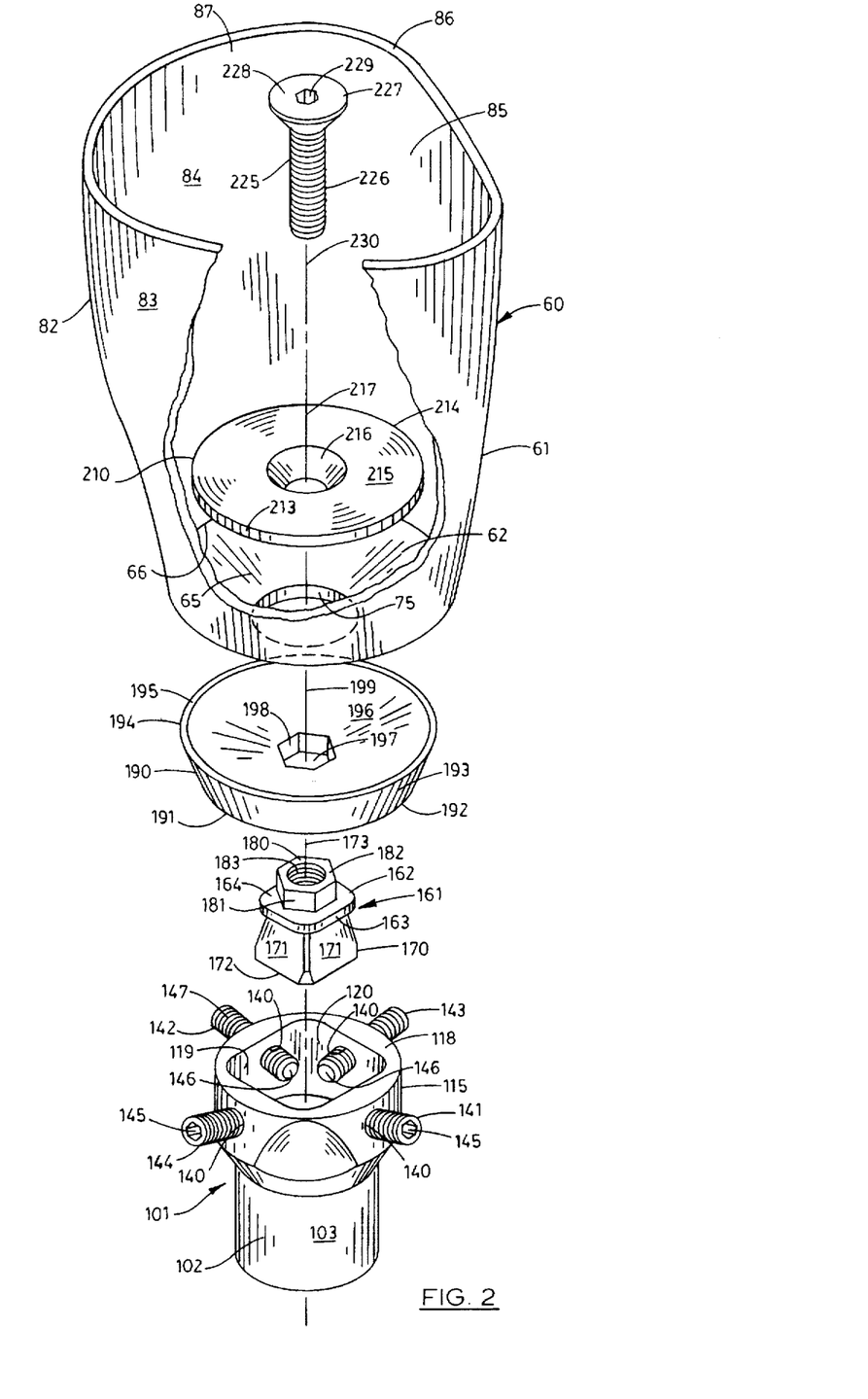
FIG. 2 is a somewhat enlarged fragmentary exploded view of the mounting apparatus of FIG. 1.
Figure 6:
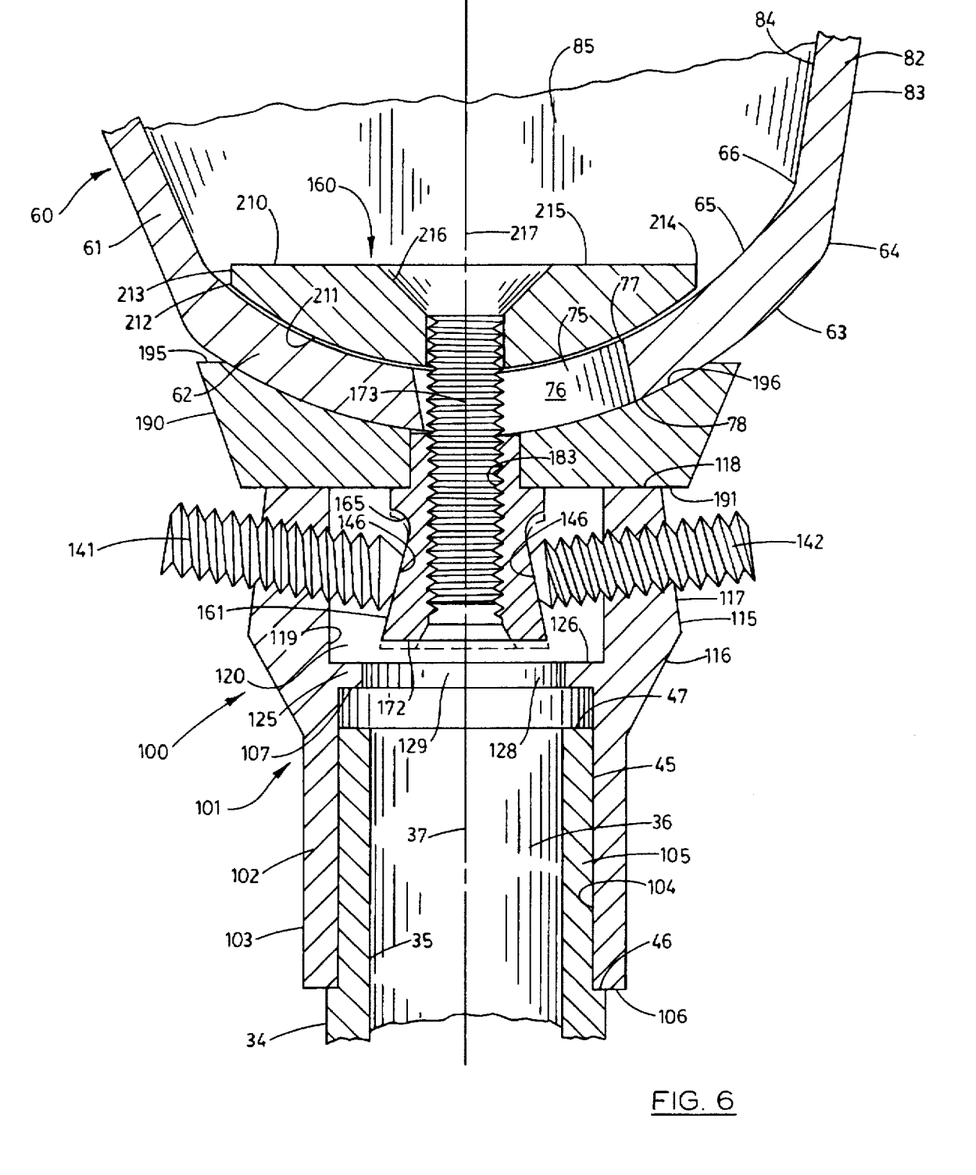
FIG. 6 is a still further enlarged, fragmentary, vertical section of the mounting apparatus as shown in FIG. 5 and showing the space between the securing plate and the base wall of the socket assembly, after loosening, permitting angular adjustment of the socket assembly relative to a prosthesis, not shown.

Four (4) internally screw threaded bores 140 extend through the portion 115 of the adjustment housing 101 and into communication with the chamber 120 therewithin. As best shown in FIGS. 2 and 6, the internally screw threaded bores are spaced from each other in a horizontal plane ninety degrees (90°) apart and, in a vertical plane, are disposed at corresponding acute angles relative to a horizontal plane, as best shown in FIG. 6. Referring more particularly to FIG. 2, an anterior adjustment screw 141 is screw-threadably received in the screw threaded, bore 140 on the lower right, as shown therein. Similarly, a posterior adjustment screw 142 is screw-threadably received in the screw threaded bore on the upper left, as viewed in FIG. 2. A medial adjustment screw 143 is screw-threadably received in the screw threaded bore 140 on the upper right, as viewed in FIG. 2. A lateral adjustment screw 144 is screw-threadably received in the screw threaded bore 140 on the lower left, as viewed in FIG. 2. Thus, it will be seen that each of the adjustment screws is individually screw-threadably adjustable along the longitudinal axis thereof within its respective screw threaded bore and inwardly or outwardly relative to the longitudinal axis 37 within the chamber 120. Each of the adjustment screws has an hexagonal socket 145 in the outer end thereof for use in the insertion of an hexagonal wrench therewithin for purposes of adjusting the adjustment screw inwardly or outwardly. Each adjustment screw has an engagement surface 146 preferably disposed at the angle, shown in FIG. 6. Each of the screws has external screw threads 147 and extends along a longitudinal axis 148 along which the adjustment screw is adjusted, as heretofore described.

The mounting apparatus 10 has a clamping assembly generally indicated by the numeral 160 and, perhaps, best shown in FIG. 2. The clamping assembly includes an adjustment body or member 161 having a central flange 162 extending outwardly thereabout to a peripheral edge 163 extending thereabout. The flange has a flat upper surface 164 and an opposite lower surface 165.

The adjustment member 161 has a lower portion 170 extending downwardly from the lower surface 165 of the central flange 162. The engagement member has four (4) sloped engagement surfaces 171 extending outwardly and downwardly to a lower surface 172. The adjustment member has a longitudinal axis 173. The lower surface 172 defines a plane right-angularly related to the longitudinal axis 173. The engagement surfaces 171 are disposed in two pairs on opposite sides of the longitudinal axis defining corresponding planes which converge at corresponding angles toward the lower surface 165 of the central flange 162, as best shown in FIGS. 2 and 6. Thus, it will be seen that the four engagement surfaces, when viewed in a plane right-angularly related to the longitudinal axis 173 of the adjustment member, are disposed at right angles to each other about the longitudinal axis.

The adjustment member 161 has an upper portion 180 extending upwardly from the upper surface 164 of the central flange 162. The upper portion has a hexagonal peripheral surface 181 and a flat upper surface 182 defining a plane right-angularly related to the longitudinal axis 173. An internally screw threaded bore 183 extends axially through the adjustment member concentric to the longitudinal axis 173, as may best be seen in FIG. 6.

The clamping assembly 160 further includes a base plate 190 having a flat lower surface 191 defining a plane right-angularly related to the longitudinal axis 173 and disposed in facing engagement with the upper planar surface 118 of the head portion 115 of the adjustment housing 101. The flat lower surface is bounded by a circular lower peripheral edge 192 from which extends upwardly a sloped peripheral surface 193 forming a truncated cone. The sloped peripheral surface extends to a circular upper peripheral edge 194 bounding a flat upper surface 195 defining a plane parallel to the flat lower surface 191 of the base plate. The flat upper surface extends about and bounds a concave upper hemispherical surface 196. The concave upper hemispherical surface is made of, or coated with, a substance having a high coefficient of friction. A hexagonal passage 197 extends through the base plate from the upper hemispherical surface through the flat lower surface 191. The hexagonal passage is bounded by a hexagonal surface 198. The hexagonal passage 197 is adapted slidably to receive the upper portion 180 permitting axial movement therebetween while preventing rotational movement due to the engagement of the hexagonal surfaces of the upper portion 180 and the hexagonal surface 198 bounding the passage 197. The base plate has a longitudinal axis 199. As shown in FIG. 6, the lower surface 191 of the base plate facingly engages the upper surface 164 of the central flange 162 of the adjustment member 161 as well as facingly engaging the upper planar surface 118 of the head portion 115 of the adjustment housing 101.

The clamping assembly 160 further includes a securing plate 210, best shown in FIGS. 2 and 6. The securing plate has a convex lower hemispherical surface 211 having a radius substantially equivalent to the radius of the concave interior hemispherical surface 65 of the prosthetic mounting socket 60. The lower hemispherical surface is bounded by a circular peripheral edge 212. The securing plate is bounded by a cylindrical peripheral surface 213 which extends to a circular upper peripheral edge 214. The upper peripheral edge bounds a flat upper surface 215 through which a countersunk screw hole 216 extends concentric to a longitudinal axis 217 of the securing plate. The securing plate is positioned, as shown in FIGS. 2 and 6, with the convex lower hemispherical surface 211 positioned in facing engagement with the concave interior hemispherical surface 65 of the prosthetic mounting socket.

A securing screw, or bolt, 225, having a screw threaded shaft 226 and a head 227, is extended through the screw hole 216 of the securing plate 210, the central passage 75 of the base wall 62 of the prosthetic mounting socket 60 and is screw-threadably received in the internally screw threaded bore 183 of the adjustment member 161 so as to link the securing plate, mounting socket, base plate 190 and adjustment member 161, as shown in FIG. 6. The securing screw has a flat upper surface 228 in which is provided an hexagonal recess 229 for receipt of an hexagonal wrench, not shown. The securing screw has a longitudinal axis 230.

Figure 5:
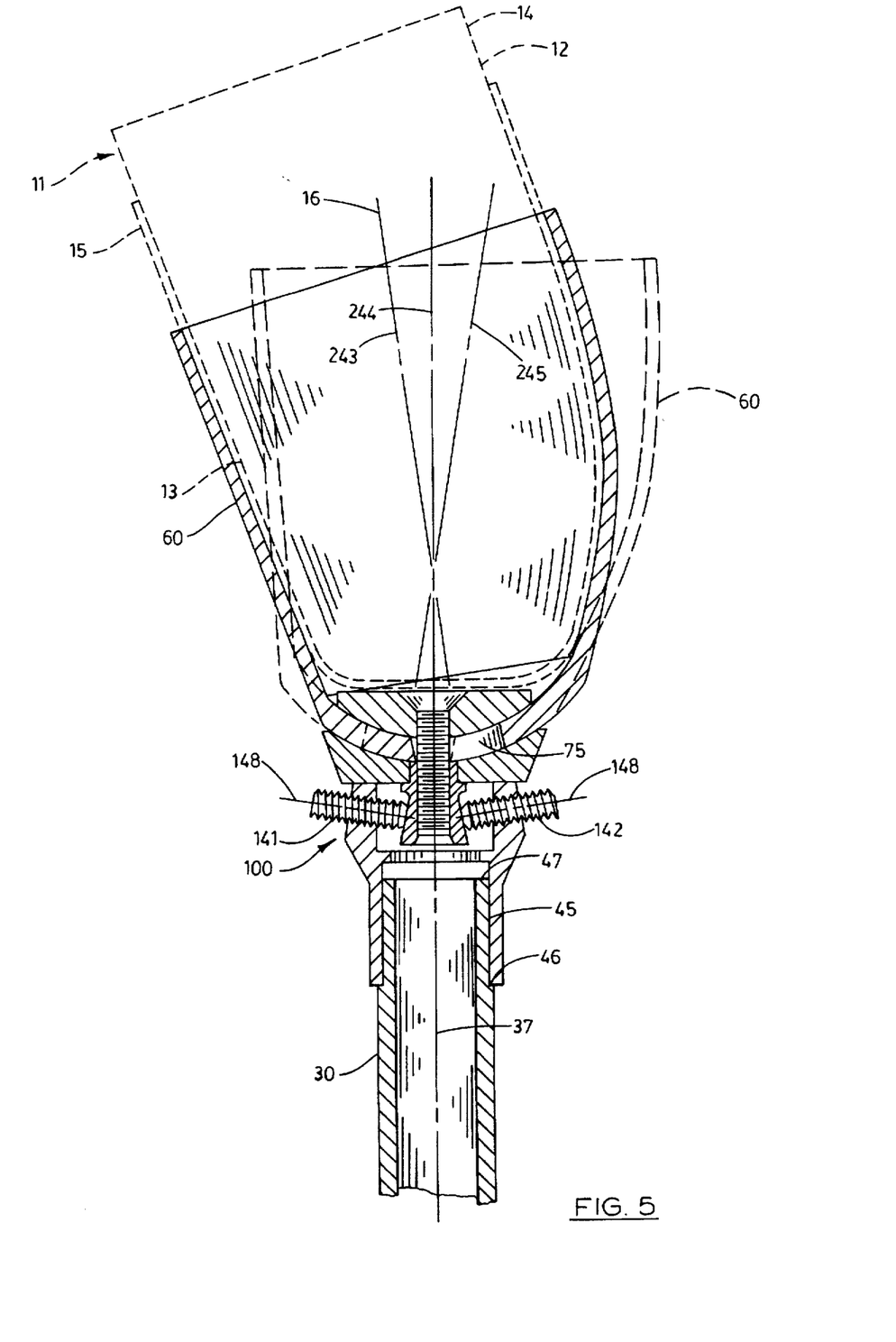
FIG. 5 is a somewhat enlarged, fragmentary, vertical section taken on line 5—5 in FIG. 1.

The mounting apparatus 10 is assembled, as shown in FIGS. 2 and 6, as heretofore described. The lower portion 170 of the adjustment member 161 is received in the chamber 120 of the head portion 115 of the adjustment housing 101 and is held in this position by the engagement of the anterior, posterior, medial and lateral adjustment screws 141, 142, 143 and 144, individually, engaging their respective engagement surfaces 171, as shown in FIGS. 4, 5 and 6.

Figure 3:
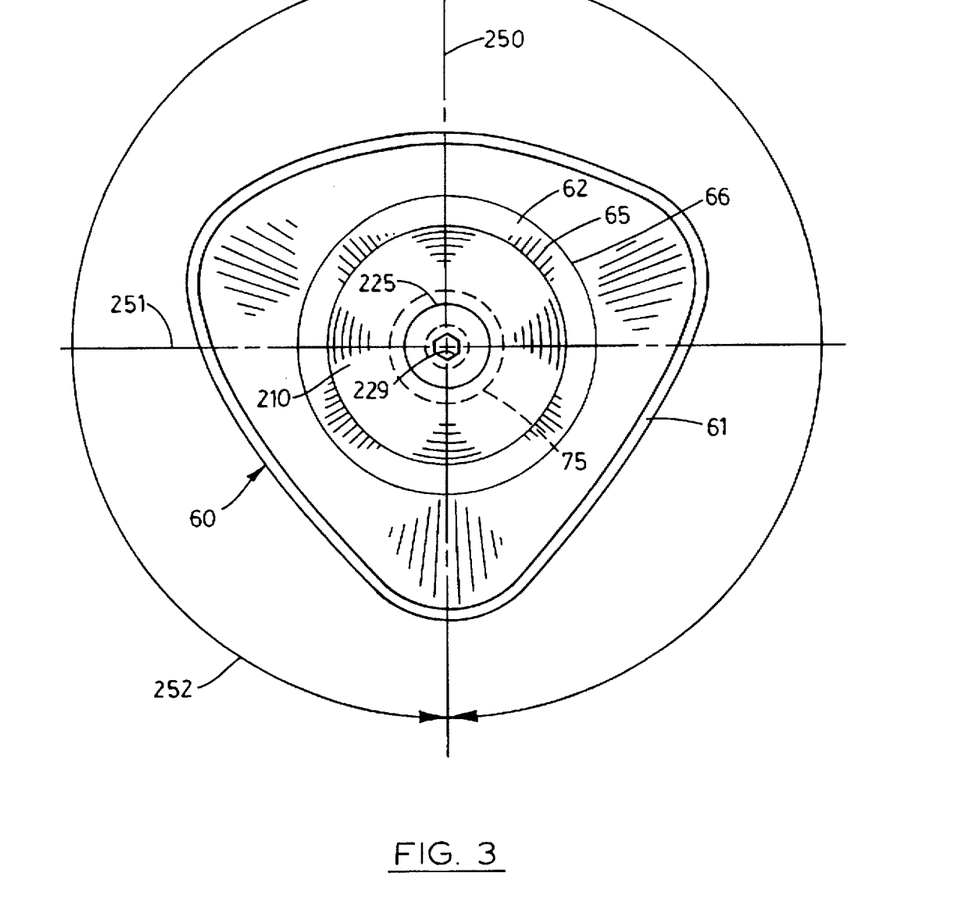
FIG. 3 is a top plan view taken on line 3—3 in FIG. 1.

For illustrative convenience, and as will hereinafter be described in greater detail, in FIG. 4 are depicted a first vertical axis of reference 240, a second vertical axis of reference 241 and a third vertical axis of reference 242. Similarly, in FIG. 5, for illustrative convenience, are shown a fourth vertical axis of reference 243, a fifth vertical axis of reference 244 and a sixth vertical axis of reference 245. Referring more particularly to FIG. 3, for illustrative convenience, are shown therein a first horizontal axis of reference 250 which is coincident with the longitudinal axes 37, 173, 199 and 217. A second horizontal axis of reference is generally indicated by the numeral 251 and is right-angularly related to the first horizontal axis of reference. The second horizontal axis of reference is also coincident with the longitudinal axes 37, 173, 199 and 217. For illustrative convenience, reference arrows 252 define a three hundred and sixty degree (360°) range of adjustment of the mounting apparatus about the longitudinal axes, as will hereinafter be described in greater detail.

OPERATION

The operation of the described embodiment of the subject invention is believed to be clearly apparent and is briefly summarized at this point.

The mounting apparatus 10 is assembled, as heretofore described. Depending upon the preference of the manufacturer, the mounting apparatus can initially be adjusted at the factory to rough settings, or to precise settings, prior to delivery. Alternatively, the mounting apparatus can simply be left in a loosely assembled, or unassembled, form in accordance with the preferences of the parties involved. In any case, whether the mounting apparatus is initially set to prescribed tolerances, or is left simply loosely assembled, the mounting apparatus may require readjustment over the period of usage thereof, or precisely to fit the requirements of the individual who wears the prosthesis. For illustrative convenience, this installation and adjustment will be described as in an initial installation. However, it will be understood that the procedures by which adjustment of the mounting apparatus takes place apply equally to all adjustment or readjustment of the mounting apparatus.

In this illustrative description, it will be understood that the mounting apparatus 10 is assembled as heretofore described and is being installed on a person requiring adjustment to the prescribed tolerances, as well as to conform to the preferences of the person wearing the prosthesis. The sleeve 15 is drawn firmly about the terminus 13 of the leg 12 into a position tightly, but comfortably, conforming to the terminus of the leg. The mounting socket 60 is then drawn about the sleeve 15 so as to conform thereto and to the terminus of the leg.

At this time the linking assembly 100 of the mounting apparatus 10 is in the assembled relationship shown in FIG. 6. More specifically, the concave upper hemispherical surface 196 of the base plate 190 engages the convex exterior hemispherical surface 63 of the mounting socket 60 so that there is no play therebetween. However, the securing screw 225 is loose enough to permit the base plate to slide thereon. The adjustment screws 141, 142, 143 and 144 are, at this time, in tightened engagement with their respective engagement surfaces 171 to retain the linkage assembly in the assembled arrangement shown in FIG. 6.

At this time, the prosthesis, not shown, mounted on the lower end portion 33 of the tubular shaft 31 is, with the mounting apparatus 10, aligned for use. The specific alignment desired and the tolerances to which the prosthesis is to be adjusted is dependent upon the multiplicity of considerations heretofore described and do not constitute part of the present invention. However, the process by which such adjustment is achieved using the mounting apparatus does constitute subject matter of the present invention and can be performed as hereinafter described.

In order to move the mounting socket 60 medially, the medial adjustment screw 143 is loosened, the adjustment is made and subsequently the lateral adjustment screw 144 is tightened inwardly again to secure the medial and lateral adjustment screws in the tightened configuration shown in FIG. 4. It will be understood that such adjustment of the mounting socket 60 simply moves the mounting socket and prosthesis through positions of parallelism to each other to achieve the precise alignment desired. The foregoing process is reversed in order to move the mounting socket 60 laterally through positions of parallelism. During this alignment process, the anterior adjustment screw 141 and posterior adjustment screw 142 are retained in tightened positions which prevents the angulation of the mounting socket from changing.

Similarly, the anterior and posterior alignment of the mounting socket 60 is achieved by adjusting the anterior and posterior adjustment screws 141 and 142, as just described relative to the medial and lateral adjustment screws 143 and 144. During such adjustment, the medial and lateral adjustment screws 143 and 144 are retained in tightened positions so as to prevent the angulation of the mounting socket from changing.

The angulation of the mounting socket 60 is changed, or adjusted, by loosening any two (2) of the adjustment screws 141, 142, 143 and 144 which are immediately adjacent to each other. For example, the anterior adjustment screw 141 and the medial adjustment screw 143 can be loosened for this purpose. This operation disengages the adjustment member 161, or more specifically the engagement surfaces 171 thereof, from the adjustment screws and permits the mounting socket to be adjusted as to angulation since the securing plate is thereby loosened. When the desired angulation has been achieved, the loosened adjustment screws are simply retightened into individual engagement with their respective engagement surfaces 171 again to lock the mounting socket into the adjusted angulation relative to the prosthesis. During this procedure, the mounting socket's selected lateral deviation remains unaffected, even though the angulation is changed, because the adjustment member is again returned to its selected position against the two (2) adjacent adjustment screws which have not been moved.

The first, second, third, fourth, fifth and sixth vertical axes of reference 240 through 245 are shown in FIGS. 4 and 5 simply to illustrate some of positions of angulation of the mounting socket in two different planes of adjustment. The first and second horizontal axes of reference illustrate the range of adjustment through three hundred and sixty degrees (360°) about the longitudinal axes of the various components of the mounting apparatus.

Once proper alignment and angulation has been achieved through the foregoing procedures, all screws and bolts are tightened down to the torque settings prescribed so as permanently, but adjustably, to be secured in their relative positions. The prosthesis is thus ready for use.

The mounting socket 60 is retained in position by clamping of the base wall 62 of the mounting socket 60 between the securing plate 210 and the concave upper hemispherical surface 196 of the base plate 190 which has, as previously specified, a high coefficient of friction. This obviates the use of set screws, as in conventional devices, and thus facilitates the adjustment of the mounting apparatus. Similarly, since the adjustment screws 141, 142, 143 and 144 are set at angles relative to the angled engagement surfaces 171 of the adjustment member 161, tightening of the adjustment screws draws the securing plate more tightly into engagement with the concave interior hemispherical surface 65 of the base wall 62 of the mounting socket and against the concave upper hemispherical surface 196 of the base plate. The mounting socket is thus firmly held in position without the use of set screws.

The adjustment member 161, as previously noted, interfits with the hexagonal passage 197 of the base plate so as to permit such sliding axial motion while preventing rotation between the adjustment member and the base plate or mounting socket. This retains the selected adjustments of the mounting socket and prosthesis which permitted the aforementioned tightening procedure.

Still further, as can best be visualized in FIG. 6, this sliding adjustment is much nearer to the mounting socket 60 than in conventional devices and the radius of movement is much greater so that adjustment for angulation does not cause so much lateral translation of the upper portion of the mounting socket relative to the longitudinal axis of the mounting assembly. When adjustment for angulation is desired, as previously noted, only two (2) of the adjustment screws need to be loosened so as to loosen the base wall of the mounting socket from the high friction surface of the concave upper hemispherical surface 196 for such adjustment. This relieves tension on the securing screw 225 and allows such angular adjustment. Subsequently by retightening the two (2) adjustment screws, the precise same selected lateral deviation is achieved with respect to the mounting socket and the remainder prosthesis.

Finally, the distance between engagement of the adjustment screws with their respective engagement surfaces 171 and the high friction surface of the concave upper hemispherical surface 196 is substantially less than in conventional devices. This allows for usage of the mounting apparatus in applications where there is little distance between the foot of the prosthesis and the terminus 13 of the leg 12. Additionally, this makes the resulting lever arm shorter so that the mounting apparatus is stronger than in conventional devices.

Therefore, the mounting apparatus of the present invention is particularly well suited to usage in the uniting of a pair of work objects in fixed relation to each other while being readily adjustable relative to a plurality of individual axes of reference; is particularly well suited to usage in environments such as the attachment and precise adjustment of prostheses; permits adjustment of the prosthesis relative to the appendage upon which it is being mounted relative to a plurality of individual axes of reference rapidly, dependably and within a range of tolerances not heretofore achieved; can be employed to maintain a given set of settings during usage over a prolonged period of time under the forces commonly experienced in such usage; is of light weight and easily manipulated in the process of attachment, adjustment and removal; and is otherwise entirely successful in achieving its operative objectives.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. An apparatus for mounting a prosthesis on an appendage of the human body, the apparatus comprising A. a socket assembly having a chamber dimensioned to receive said appendage therewithin oriented so as substantially to retain said socket assembly and appendage in substantially fixed relation to each other and relative to a longitudinal axis of the appendage and bounded at a lower end by a base wall through which a passage extends and having a concave, substantially hemispherical interior surface facing said chamber and a convex substantially hemispherical exterior surface;

B. a housing adapted to be mounted on the prosthesis in fixed relation to a longitudinal axis thereof, having a substantially flat bearing surface defining a plane of reference substantially right-angularly related to said longitudinal axis of the appendage and an internal chamber communicating with said bearing surface of the housing;

C. a base plate having a substantially flat bearing surface disposed in facing engagement with said bearing surface of the housing substantially right-angularly related to said longitudinal axis of the appendage for slidably adjustable movement thereacross, a concave, substantially hemispherical surface on the opposite side thereof from said bearing surface having a high coefficient of friction disposed in facing engagement with the convex substantially hemispherical surface of the base wall of said socket assembly and a passage extending through said base plate interconnecting said hemispherical surface and bearing surface and having a predetermined transverse configuration;

D. a securing plate having a convex, substantially hemispherical surface disposed in facing engagement with the concave, substantially hemispherical surface of the base wall of the socket assembly within said chamber thereof and having a screw hole extending therethrough;

E. a linking assembly including an adjustment body disposed in said internal chamber of said housing having a screw threaded bore extending axially therethrough defining a longitudinal axis, an upper portion substantially axially related to said longitudinal axis and having a transverse configuration adapted to be received in said passage of the base plate permitting axial movement therewithin while preventing movement about said longitudinal axis, a flange disposed in facing engagement with said bearing surface of the base plate and a lower portion having four engagement surfaces disposed at corresponding acute angles relative to the bearing surface of the base plate and each facing in a direction substantially ninety degrees (90°) about said longitudinal axis from the adjacent engagement surfaces and a screw extended through the screw hole of the securing plate, the passage of the base wall of the socket assembly and screw threadably received in said screw threaded bore of the adjustment body to capture the base wall of the socket assembly between the hemispherical surface of the securing plate and the hemispherical surface of the base plate; and F. four adjustment screws individually screw-threadably extending into said housing and into the internal chamber thereof into individual engagement with the engagement surfaces of the adjustment body and being disposed, relative to the longitudinal axis of said adjustment body, at corresponding acute angles such that screw threaded adjustment of said adjustment screws is operable to adjust said socket assembly relative to said longitudinal axis of the appendage and inward screw threaded adjustment of the adjustment screws draws said securing plate and thereby the base wall of the socket assembly into fixed relation relative to the base plate.

2. The apparatus of claim 1 wherein said screw of the linking assembly has a smaller transverse dimension than the corresponding transverse dimension of said passage of the base wall of the socket assembly whereby loosening of said screw of the linking assembly permits the socket assembly to be angularly repositioned relative to said longitudinal axis of the prosthesis to a new attitude and to be secured in said new attitude by again tightening said screw in the screw threaded bore of the adjustment body.

* * * * *

UNITED STATES PATENT AND TRADEMARK OFFICE
CERTIFICATE OF CORRECTION

PATENT NO. : 5,759,206
DATED : June 2, 1998
INVENTOR(S) : David E. Bassett

It is certified that error appears in the above-identified patent and that said Letters Patent is hereby corrected as shown below:

Column 1, Line 51, delete "adjustment" and substitute
---adjustments---.

Column 4, Line 59, between "the" and "portion" insert
---head---.

Signed and Sealed this

Fourth Day of August, 1998

Attest:

BRUCE LEHMAN

*Attesting Officer*    *Commissioner of Patents and Trademarks*